(12) United States Patent
Zatezalo et al.

(10) Patent No.: US 6,339,718 B1
(45) Date of Patent: Jan. 15, 2002

(54) PROGRAMMABLE INJECTOR CONTROL

(75) Inventors: Doug Zatezalo; Jeffrey John Thompson, both of Allison Park; Steven C. Rygg, Irwin; Scott R. Griffith, Delmont; John Gardner, Wexford; Ronald Barbati, Pittsburgh, all of PA (US)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 09/365,278

(22) Filed: Jul. 30, 1999

(51) Int. Cl.$^7$ .............................. A61B 6/00; A61M 5/00
(52) U.S. Cl. .................. 600/432; 604/92; 604/232; 604/246; 604/247; 604/281; 604/154; 604/131; 604/65; 604/66; 604/67; 604/27; 604/134
(58) Field of Search ................................. 600/432, 410, 600/420, 3, 4, 5; 604/92, 232, 246, 247, 281, 154, 131, 65, 66, 67, 27, 134

(56) References Cited

U.S. PATENT DOCUMENTS 3,888,239 A * 6/1975 Rubinstein .................. 600/432
5,472,403 A * 12/1995 Cornacchia et al. ........... 600/4
5,494,036 A * 2/1996 Uber, III et al. ............ 600/432

OTHER PUBLICATIONS

Optistar MR Injector System 510(k) Summary (Nov. 4, 1998).
Opristar MR Contrast Delivery System Brochure (2000).
Optistar MR Digital Injection System Operator's Manual, 801900–A (Nov. 1999).
MR Sonic Shot 50 Operator's Manual (with Accompanying English Translation of Chapter 11), Ver.2.0.0 (Dec. 24, 1999).
Injektron 82 MRT User Instructions, Version MR 2 ( Mar. 10, 1999).
Medrad Vistron CT Injector System Operation Manual; pp. 21–26 (2000); 95403–T–141, Rev. B.

* cited by examiner

Primary Examiner—Marvin M. Lateef
Assistant Examiner—Jeoyuh Lin
(74) Attorney, Agent, or Firm—Ian K. Samways; George L. Bradley (57) ABSTRACT

A fluid injection arrangement, in the context of patient imaging systems, in which phases of contrast medium injection and flushing medium injection can be freely and selectably ordered so as to make available to the operator and patient a vast array of possible protocols that has hitherto been essentially unattainable. Also contemplated is the use of a "hold" phase, involving an indefinite pause between phases of a protocol, in connection with such imaging systems. Further contemplated is the use of a "pause" phase in which a pause of fixed duration is pre-programmed into the protocols of MRI injector systems.

80 Claims, 6 Drawing Sheets

PROGRAMMABLE INJECTOR CONTROL

FIELD OF THE INVENTION

The present invention generally relates to powered injectors and syringes for use therewith, and more particularly, to methods and apparatus for automatically controlling the same.

BACKGROUND OF THE INVENTION

A number of injector-actuated syringes and powered injectors for use in medical procedures such as angiography, computed tomography, ultrasound and NMR/MRI have been developed. U.S. Pat. No. 4,006,736, for example, discloses an injector and syringe for injecting fluid into the vascular system of a human being or an animal. Typically, such injectors comprise drive members such as pistons that connect to a syringe plunger. For example, U.S. Pat. No. 4,677,980, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858.

U.S. Pat. No. 5,494,036 discloses a patient infusion system adapted for use in MRI. The infusion system is designed to be substantially non-reactive with the magnetic field generated by the magnetic resonance imaging system for producing diagnostic images.

Medrad has also developed a control arrangement ("SPECTRIS") for an MRI infusion system that uses two syringes, namely, one for the introduction of contrast medium into a patient and the other for a flushing medium. As is known conventionally, it is often desirable to flush from the tubing of an infusion system a residual quantity of contrast medium that remains there after a given infusion procedure, as contrast medium tends to be expensive and its efficient use, without waste, is often seen as a top priority. The "SPECTRIS" control arrangement will thus not only account for the residual contrast medium left in the tubing, and aim to use it in an infusion procedure, but will utilize a much cheaper flushing medium, such as a saline solution, in order to serve the purpose of pushing the residual contrast medium through the tubing and even through the patent's body (so as to "push" and deliver contrast medium to a region of interest in the body). Other advantageous purposes have also been recognized in connection with such flushing media, such as maintaining a flow through the patient's veins for a predetermined period of time in order that the veins will be better prepared to subsequently receive a new infusion of contrast medium.

The "SPECTRIS" control arrangement is a pre-programmable arrangement for establishing a precise protocol for the infusion of contrast medium followed by flushing medium. At the time that the "SPECTRIS" system was established, needs in the industry were generally such that only some very simple protocols were desired. Thus, the "SPECTRIS" system addressed such needs by permitting protocols in which one or two "phases" of contrast medium took place followed by zero, one or two "phases" of flushing medium infusion. "Phase" refers to the application of a given quantity of a given medium at, for example, a fixed flowrate for a fixed period of time. Thus, up to two phases each of contrast medium and flushing medium, for example, were permitted by the "SPECTRIS" system, in order to provide a patient with different modes of infusion one after the other to serve particular purposes.

Of late, however, some disadvantages have been noted in connection with the "SPECTRIS" control system and other related systems. Not the least of these is the lack of flexibility in developing and administering infusion protocols to a patient, as the "SPECTRIS" system would allow no more than two distinct phases for each medium, and no single phase of flushing medium infusion could take place between two different phases of contrast medium infusion.

A further disadvantage has been recognized in that the aforementioned phases will typically be administered one after the other without the opportunity for an intermediate pause or hold between phases. This would appear to limit the convenience and utility of the system in question in many respects.

Nemoto and Co., Ltd., of Tokyo, Japan has also developed a control system for an MR injector. However, this appears to be even less flexible than the "SPECTRIS" system in that only protocols consisting of no more than one contrast medium infusion and no more than one flushing medium infusion appear to be permitted.

In the realm of CT (computed tomography) injection technology, Medrad has developed the "ENVISION" control system. As flushing media have generally not been hitherto employed in CT injector systems, the "ENVISION" system, much as any conventional CT injector control system, contemplates only the use of a single syringe for patient infusion, and solely for use with contrast medium. The "ENVISION" system permits protocols that employ up to eight different phases of contrast medium infusion, wherein each phase may employ a different infusion flowrate, infusion quantity and/or infusion duration. Pre-programmed pauses between infusion phases are also conceivable within such a context.

Evolving needs have thus been recognized in connection with providing an injection control system that is much more readily adaptable to a wider range of contexts.

SUMMARY OF THE INVENTION

Generally, at least one presently preferred embodiment of the present invention broadly contemplates a fluid injection arrangement, in the context of patient imaging systems, in which phases of contrast medium injection and flushing medium injection can be freely and selectably ordered so as to make available to the operator and patient a vast array of possible protocols that has hitherto been essentially unattainable.

The present invention also broadly contemplates the use of a "hold" phase, involving an indefinite pause between phases of a protocol, in connection with such imaging systems.

Also broadly contemplated herein is the use of a "pause" phase in which a pause of fixed duration is pre-programmed into the protocols of MRI injector systems.

BRIEF DESCRIPTION OF THE DRAWINGS

The present invention and its presently preferred embodiments will be better understood by way of reference to the detailed disclosure herebelow and to the accompanying drawings, wherein.

DESCRIPTION OF THE PREFERRED EMBODIMENTS

Figure 1:
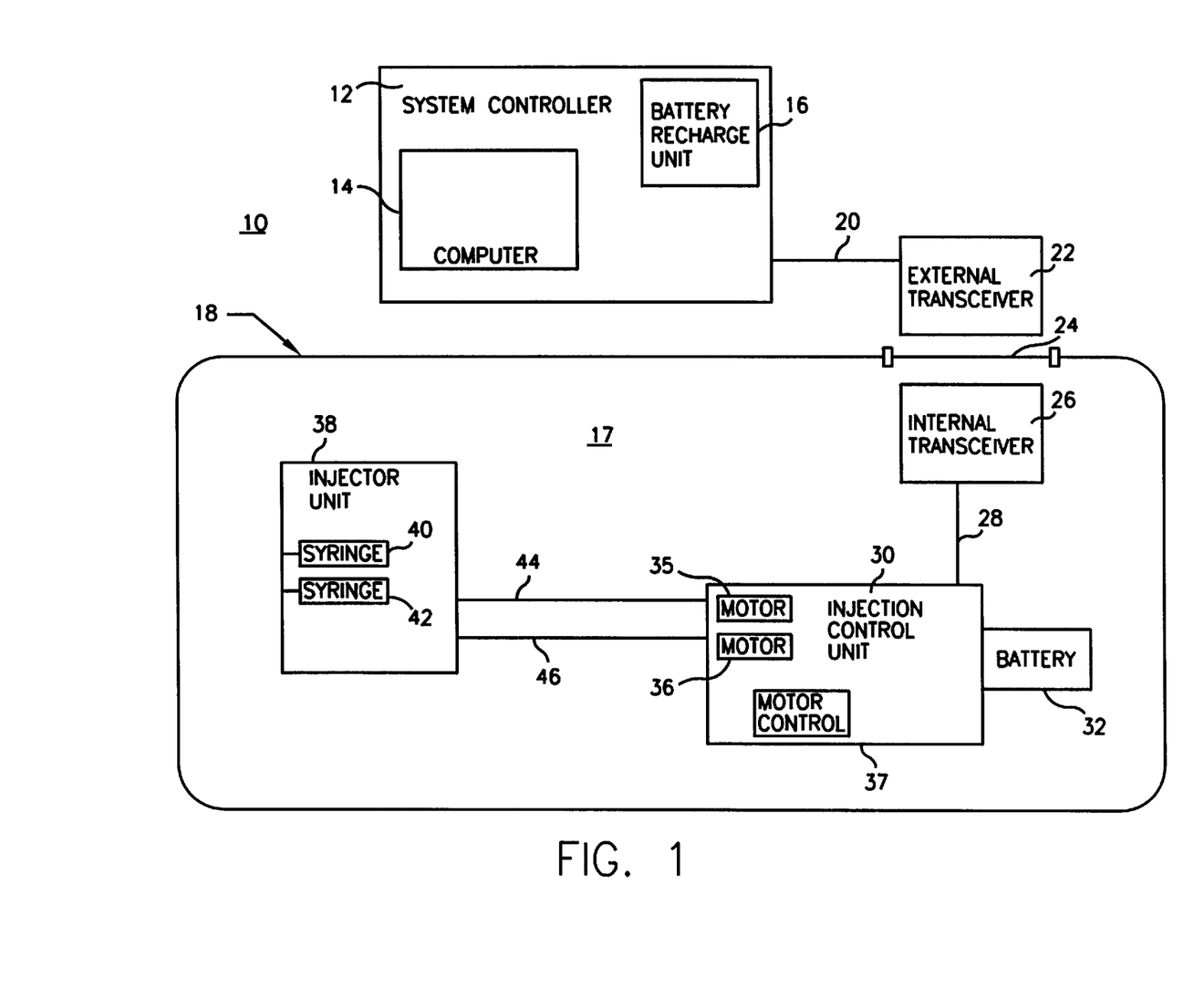
FIG. 1 is a schematic depiction of a conventional magnetic resonance imaging (MRI) injector system arrangement.
Figure 2:
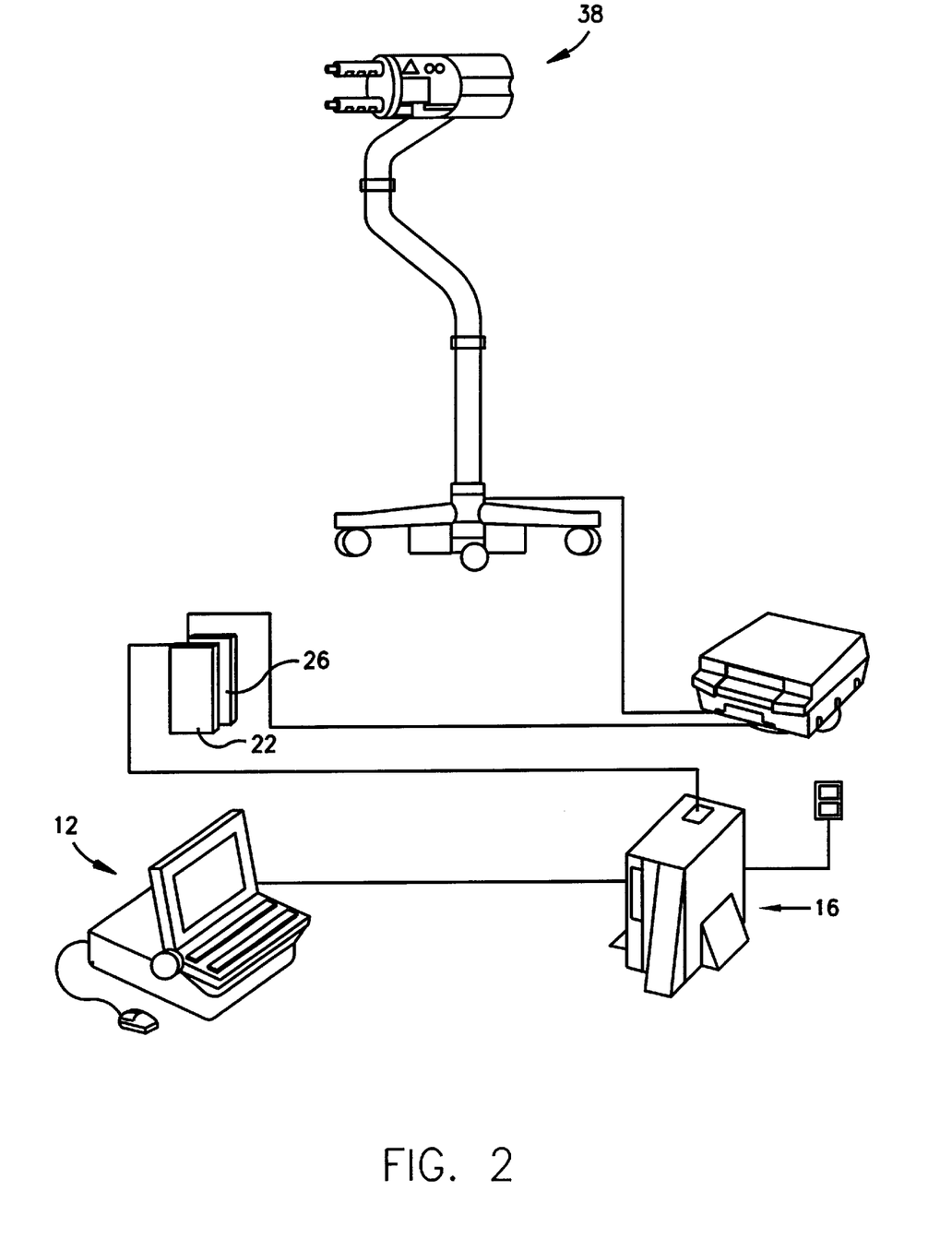
FIG. 2 is a pictographic depiction of a conventional MRI injector system arrangement.

FIGS. 1 and 2 generally illustrate a conventional MRI injector system arrangement, such as is disclosed in U.S. Pat. No. 5,494,036 to Uber et al, the contents of which are incorporated herein by reference. A magnetic resonance injector system is shown generally at 10. The MRI system includes a system controller 12 which incorporates a computer 14 and a battery charging unit 16. The system controller 12 is located externally of the imaging room 17, the imaging room being shielded from electromagnetic interference by a shield 18.

Isolation can be achieved by completely enclosing the room with copper sheet material or some other suitable, conductive layer such as wire mesh. Communication line 20, connects the system controller 12 with an external infrared/optical communications transceiver 22. The shielded imaging room 17 also incorporates a patient viewing window 24 in the shield 18 which allows an operator to view the imaging room. The window 24 can be formed by sandwiching a wire mesh material (not shown) between sheets of glass or coating the window with a thin coating of conductive material such as gold (not shown) to maintain the continuity of the electromagnetic shield 18.

An infrared/optical communications transceiver 26 is positioned internally of the imaging room 17 at the viewing window 24 opposite the external communications transceiver 22 such that the internal and external communications transceivers communicate with each other through the viewing window with no breach of the electromagnetic shield. A communications link 28 located within the shielded area connects the internal infrared/optical transceiver with an injection control unit 30. The injection control unit 30 is powered advantageously by rechargeable battery 32. The injection control unit 30 also incorporates control circuitry which controls electric motors 35, 36 which are also located within the injection control unit. The injection control unit is contained within an electromagnetic shield 37 to prevent interference with the magnetic field used to generate the magnetic resonance image.

The injection head unit should preferably be located in close proximity to the patient in order to decrease the distance that the contrast media fluid must travel from the contrast media injectors. The injection head unit 38 includes contrast media injection syringe and piston units 40, 42. The syringes 40, 42 are in operation communication with the electric motors in the injection control unit by flexible mechanical drive shafts 44, 46, respectively. The drive shafts are preferably made from a nonferrous metal such as hard brass.

The disclosure now turns to an embodiment of the present invention, as illustrated in FIGS. 3–6, that could conceivably be employed in connection with a MRI injector system such as that shown in FIGS. 1 and 2 or with any other of a wide range of MR, CT, angiographic or ultrasound injector systems. These possible uses of at least one embodiment of the present invention are elucidated in greater detail herebelow.

Shown schematically in FIGS. 3–6 are various incarnations of a touch screen arrangement 200 that could be employed in accordance with at least one presently preferred embodiment of the present invention. As a non-restrictive example, such a touch screen arrangement could be utilized in conjunction with a system controller 12 and computer 14 such as that described and illustrated hereinabove with respect to FIGS. 1 and 2. While a touch screen arrangement is contemplated in connection with FIGS. 3–6, it is to be understood that other types of data entry arrangements are conceivable that would achieve an equivalent purpose. Display fields 210, 220 could also be touch fields used for desired purpose. For example, soft or hard key entry could be used, as well as trackball arrangements, mouse arrangements, or a cursor control touch pad (remote from the screen).

Figure 3:
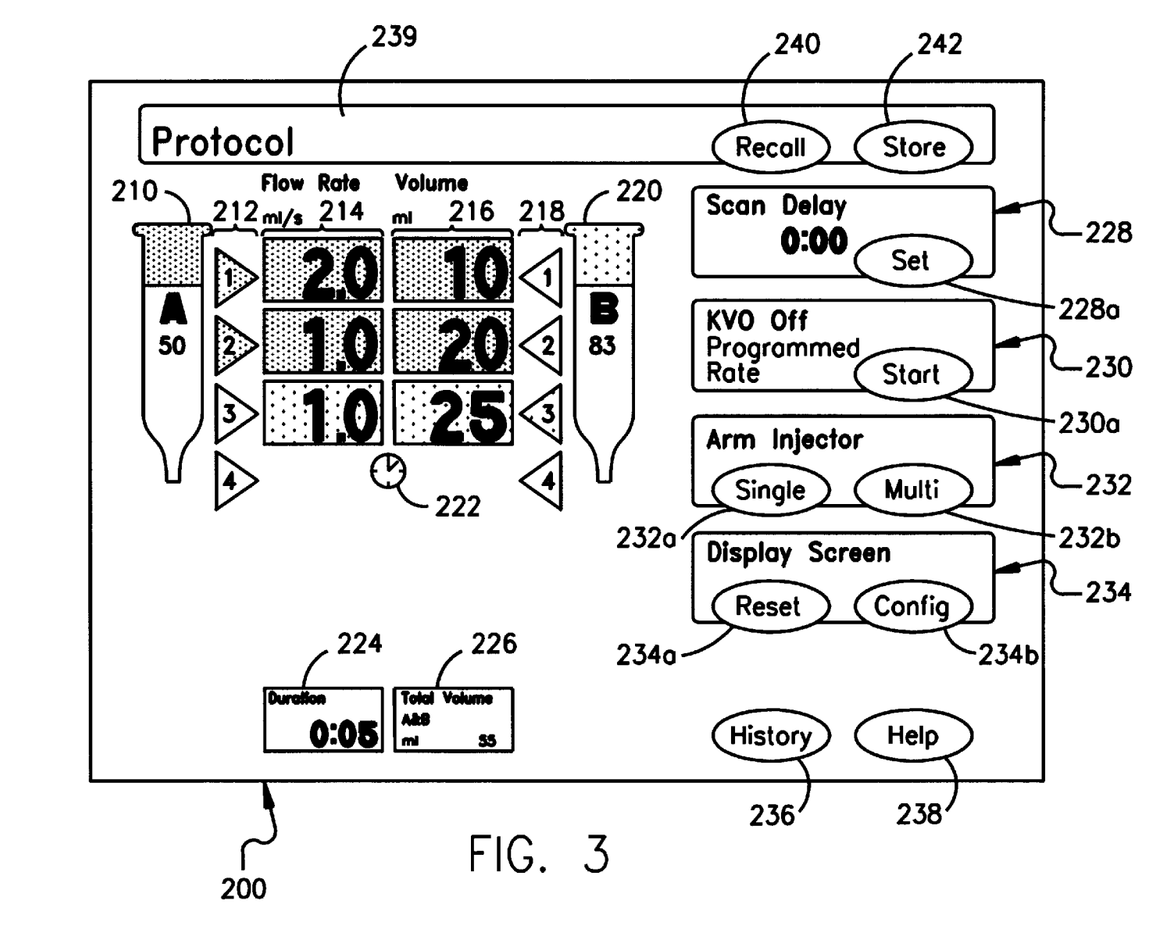
FIGS. 3–6 are various depictions of a control screen arrangement for use with different protocols.

As shown in FIG. 3, touch screen arrangement 200 may permit for the display of a display field 210 corresponding to the available quantity of contrast medium, a variable column 212 of touch fields for facilitating the entry of control parameters relating to contrast medium, a variable column 214 of touch fields relating to flowrate, a variable column 216 of touch fields relating to volume, a variable column 218 of touch fields for facilitating the entry of control parameters relating to flushing medium and a display field 220 corresponding to the available quantity of flushing medium. Display fields 210, 220 could also be touch fields used for a desired purpose.

The term "contrast medium", as employed herein, refers to essentially any suitable type of medium, as used in the medical arts, that is injected into a patient and, in the context of an imaging process (such as MR, angiography, ultrasound or CT), facilitates in highlighting selected areas of the patient's body while he/she is being scanned. In addition, the term "contrast medium", as employed herein, also refers to other diagnostic or therapeutic agents for injection into patients. The term "flushing medium", as employed herein, refers to essentially any suitable type of medium, such as a saline solution, that can be used to flush contrast medium from the tubing of an infusion system and that is well-suited for flowing through the patient's body so as to serve a useful supplementary purpose, such as keeping his/her veins open in preparation for another infusion of contrast medium.

As will be appreciated throughout this disclosure, the touch screen arrangement 200 is preferably configured for permitting the operator to freely and flexibly incorporate phases of contrast medium infusion and phases of flushing medium infusion with respect to one another in a manner that has hitherto apparently not been contemplated nor realized. (A definition of "phases" may be found in the "Background" section of this disclosure). Further, the present invention also broadly contemplates, in accordance with at least one presently preferred embodiment, optional "hold" and "pause" phases as discussed herebelow.

Accordingly, FIG. 3 illustrates one conceivable protocol that may be entered in accordance with an embodiment of the present invention. As shown, displays 210 and 220 show that 50 ml of contrast medium are available, as are 83 ml of flushing medium. Also, the operator has selected the provision of two phases of contrast medium followed by one phase of flushing medium.

Preferably, the first phase of contrast medium infusion will have been set by activating the touch field 1 in column 212, followed by activating the corresponding entry fields in columns 214 and 216 and entering in them, respectively, the desired flowrate and desired volume to be administered to the patient. The entry of data can be accomplished by touching on a touch field (214 or 216), which could prompt the appearance of a key pad on the screen that would allow the entry of specific values in the fields 214, 216.

As shown, a second phase of contrast medium infusion has also been set in similar manner, but this time by activating touch field 2 in column 212, followed by activating the corresponding entry fields in columns 214 and 216 and again entering in them, respectively, the desired flowrate and volume.

For the third phase, as shown in FIG. 3, the operator has selected a flushing medium infusion phase, this time by activating touch field 3 in column 218 and then entering the desired flow rate and volume parameters in the corresponding fields in columns 214 and 216.

The result is a three-phase protocol that will result in the administration of: (1) a first phase of contrast medium infusion (10 ml) at 2.0 ml/s; (2) a second phase of contrast medium infusion (20 ml) at 1.0 ml/s; and (3) a phase of flushing medium infusion (25 ml) at 1.0 ml/s. Such a protocol might be desirable, for example, when it is desired that a patient first receive a first, quick infusion of contrast medium of smaller volume (i.e., a bolus of contrast medium) so as to accentuate (for imaging purposes) a small, particularized part of the body where such an infusion may be desirable (e.g., the kidneys), followed by a second, slower infusion of contrast medium of larger volume (e.g., a trickle or drip of contrast medium) that would be of use in a larger part of the body where a faster flowrate might not be needed (e.g., peripheral vascular regions of the legs). The flushing phase, then, could subsequently be utilized for purposes such as those described heretofore.

In a preferred embodiment of the present invention, touch screen arrangement 200 may be so configured as to display only those data entry fields in columns 214, 216 that have been specifically activated by the operator (via activation of corresponding touch fields in columns 212, 218), so that there will be no data fields visible in columns 214, 216 corresponding to phases that are not to be used for a given protocol. Thus, FIG. 3 shows that no data fields are visible in columns 214, 216 in correspondence with a fourth phase, since only three phases are being employed. Further, there will only preferably be one touch field in columns 212 and 218 visible beyond the number of phases that has already been chosen by the operator. Thus, as shown in FIG. 3, three phases have been entered and the touch fields 4 in columns 212 and 218 are visible in preparation for possible activation of a fourth phase by the operator. In the meantime, a suitable icon 222 (preferably having use in connection with a "hold" phase, as described later) may be provided in place of the absent data entry fields in columns 214 and 216. Accordingly, it will also preferably be the case that, prior to the activation of any phases at all, at an introductory stage of the process, no touch fields in columns 212–218 will be visible at all except for the touch fields 1 in the first row.

As shown, the incrementally emerging data fields in columns 214 and 216 may assume different shades, in correspondence with the type of phase being employed. Thus, in the embodiment illustrated in FIG. 3 (as well as FIGS. 4–6), the data entry fields assume a darker shade in correspondence with a contrast medium infusion phase, while they assume a lighter shade in correspondence with a flushing medium infusion phase. Further, the numbered touch fields in columns 212 and 218 may each preferably assume a corresponding shade in accordance with their being individually activated. Thus, fields 1 and 2 in column 212 are shaded in correspondence with their having been activated in the process of setting up two contrast medium infusion phases (following from their proximity to display field 210, which corresponds to contrast medium), while field 3 in column 218 is shaded in correspondence with its having been activated in the process of setting up a flushing medium infusion phase. In contrast, neither of the fields 4 in columns 212, 218 are shaded since neither has been activated to set up a phase of any sort.

The concept of incrementally emerging data fields in columns 214, 216, as discussed above, helps illustrate the flexibility and versatility afforded in accordance with at least one presently preferred embodiment of the present invention. Particularly, in the embodiment illustrated in FIG. 3, data fields emerge only to the extent that they are needed and can apply to either a contrast medium infusion phase or a flushing medium infusion phase at the behest of the operator. Such an arrangement would appear to stand in stark contrast to those conventional arrangements, such as the "SPECTRIS" arrangement described heretofore, in which the order of phases is comparatively fixed and inflexible.

Also illustrated in FIG. 3, inter alia, are a duration display field 224 and a total volume display field 226. These preferably will serve as, respectively, a clock of elapsed time that starts from zero and spans the duration of the totality of the phases that have been entered and an indicator of the total volume of fluid (destined for the patient) that has been expended over the totality of the phases. As shown in FIG. 3, duration display field 24 also preferably shows the projected total duration before injection starts, and volume display field 226 also preferably shows, at that time, the total projected volume to be expended.

Figure 4:
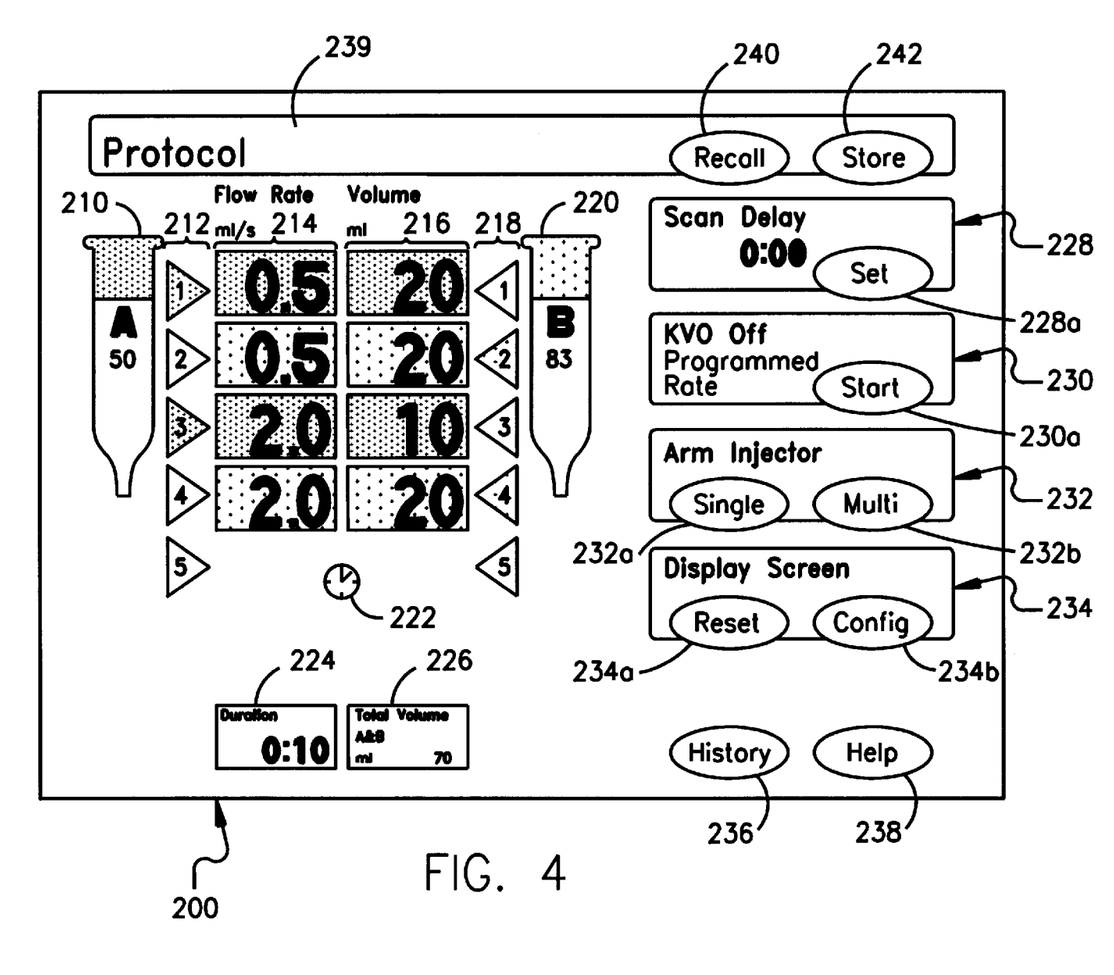
Figure 5:
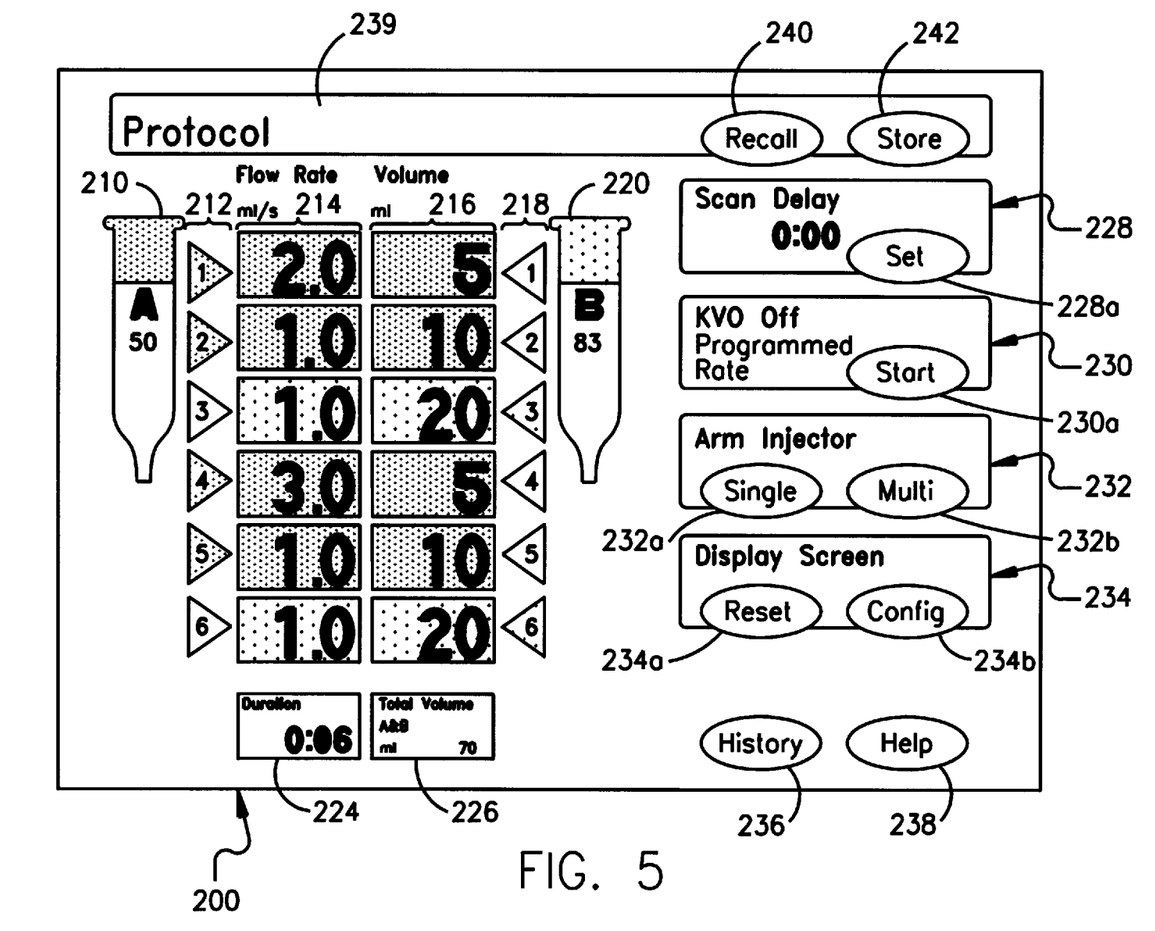
Figure 6:
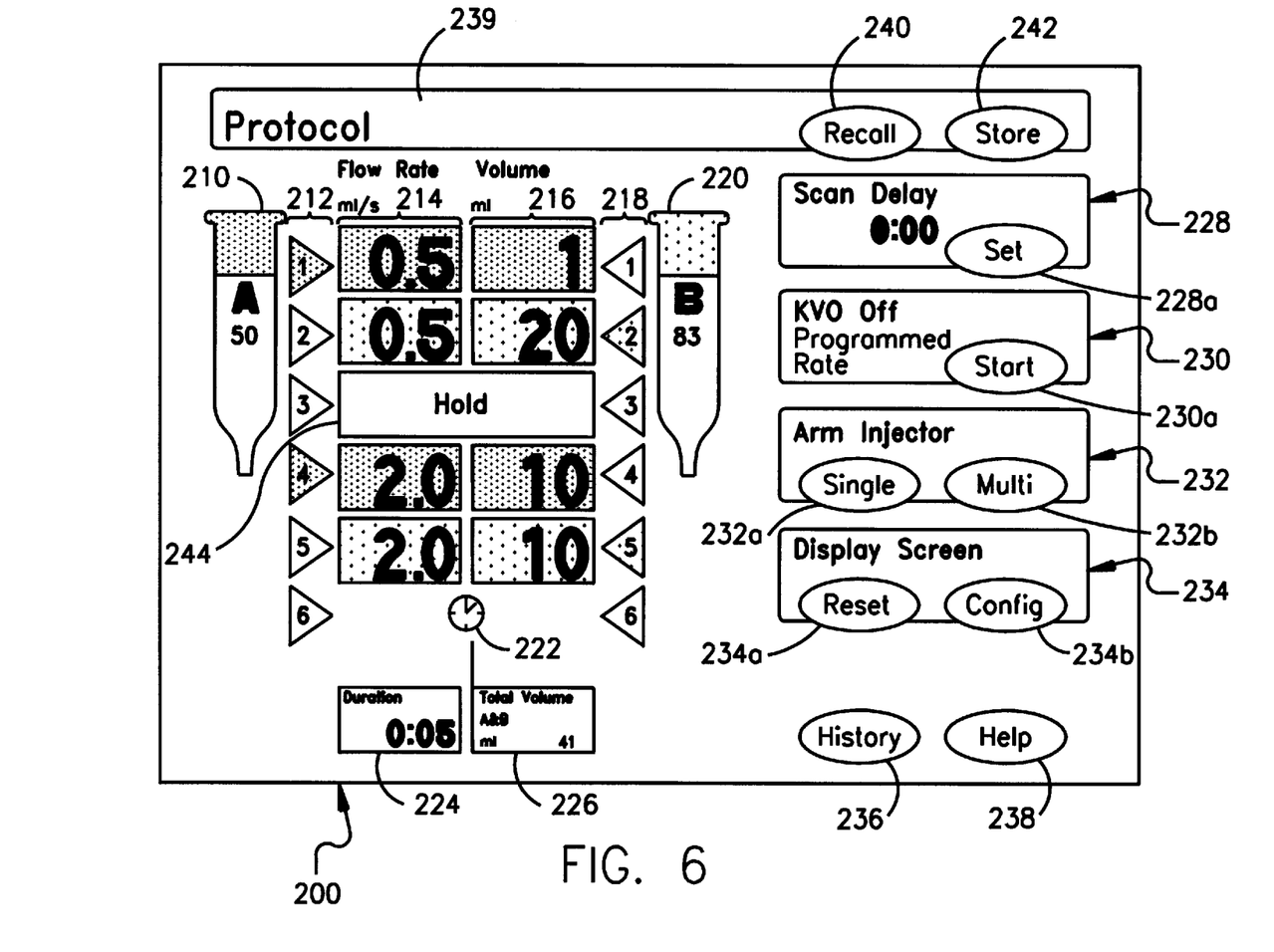

FIGS. 4–6 serve to further illustrate the versatility and flexibility afforded in accordance with at least one presently preferred embodiment of the present invention. Reference numerals in those figures relate to similar components referenced by similar numerals in FIG. 3.

In the protocol shown in FIG. 4, the operator has chosen a first phase of contrast medium infusion, followed by a first phase of flushing medium infusion, followed by a second phase of contrast medium infusion, finally followed by a second phase of flushing medium infusion.

FIG. 5 illustrates a different protocol, but this time involving six phases. Particularly, the six phases illustrated are two separate contrast medium phases, followed by a flushing medium phase, followed again by two distinct contrast medium phases, finally followed by a flushing medium phase.

Finally, FIG. 6 illustrates a protocol involving a distinct "hold" phase in accordance with an embodiment of the present invention. As shown here, the operator has selected a contrast medium phase followed by a flushing medium phase. However, the operator has also now selected a "hold" phase, indicated at 244, in which, for an indefinite period of time (possibly capped automatically for safety reasons), the regulated administration of fluids may cease. The "hold" phase may be activated on touch screen arrangement 200 by pressing on icon 222, which would then produce a "hold" display field 244 that spans both columns 214, 216. The "hold" phase is then followed by a second contrast medium phase and a second flushing medium phase.

The value of including a "hold" phase is that it permits some time for the operator to render supplementary judgements, following the administration of the phase(s) before the "hold", that could be of value when administering the phase(s) that occur(s) after the "hold". As an example, and as can be appreciated from the protocol shown in FIG. 6, the operator may wish to first infuse a short bolus of contrast medium not for imaging purposes but for the purpose of determining the length of time (by any suitable means) that the bolus requires in order to reach a given target area in the patient's body. Once a flushing phase is completed, the "hold" may then take effect. During the "hold", the imaging scanner (not shown here) could be programmed to delay its imaging action for a period of time that corresponds to the "delay" that the "short bolus" required in order to reach the target area of the body. In turn, the scan delay (i.e., the length of time that the scanner could "wait" before imaging the target area of the body) can be entered into a display field 228 by means of a touch field 228a suited for that purpose. In this manner, when the time comes to administer the second contrast medium phase, the resulting bolus will be permitted to pass through the patient's system for a length of time corresponding to the "scan delay" before the scanner, conceivably prompted automatically via the scan delay clock in field 228 or perhaps manually by the operator (for example, upon hearing an audible signal), itself is activated as to image the target area of the patient. In this manner, the scanner will be active for only such a length of time as is clearly necessary for imaging the target area, thus providing a highly desirable cost savings.

Other touch fields and display fields may be provided within touch screen arrangement 200. As shown in FIGS. 3–6, a KVO ("keep vein open") display field 230 may show the status of "KVO", that is, whether there is a circulation of flushing medium (either continuously or in small intermittent bursts) in the patient's system for the purpose of maintaining a flow of some type in his/her veins and perhaps to show a countdown of the time remaining in such a state. The duration of "KVO" could preferably be capped, in correspondence with the actual quantity of flushing medium available (minus the flushing medium required for any subsequent flushing medium phase), automatically by the control system. Thus, automatic shutoff could take place when the reservoir of available flushing medium has decreased to a point at which, with further depletion, there would not be a sufficient amount of flushing medium for a subsequent flushing medium phase or phases. It will be appreciated that "KVO" is not so much a flushing phase per se but instead is a "maintenance" phase in which the patient's veins are maintained in a relatively open state in preparation for the subsequent administration of contrast medium, or possibly even for other reasons. "KVO" could thus well take place during a "hold" phase so that, for example, the patient's veins could remain relatively open and free while the aforementioned intermediate calculations, etc., are taking place. Normally, the rate, volume and frequency of delivery in "KVO" is fixed ahead of time but it could also be variably programmed by the operator, by any suitable means.

The "arm injector" display field 232 and associated touch fields 232a and 232b serve the purpose of arming the injector and initiating the start of injection.

On the other hand, the "display screen" display field 234 and associated touch fields 234a and 234b serve the purpose of accessing any configuration (set-up) information such as language (e.g., English, German, French, Japanese, etc.) or KVO parameters or for reset (e.g. zeroing) of the screen.

The "history" display field 236 may serve the purpose of recalling past injection information that has been stored, while the "help" field 238 may serve the purpose of providing assistance to the operator in a manner similar to the "help" arrangements found on a typical computer or computer software system.

Finally, the "protocol" display field 239 and associated touch fields 240, 242 may serve the purposes of the identification, storage and recall of user-defined (saved) injection programs or (factory) pre-loaded programs.

Although the present invention, in accordance with at least one presently preferred embodiment, has been described hereinabove primarily in connection with an MR injector system, it is to be understood that other applications are possible without departing from the spirit and scope of the invention in general. For example, while it is known that CT, angiographic and ultrasound injectors to date have generally utilized only a single syringe, containing contrast medium, for administering solely contrast medium to a patient, the present invention broadly contemplates the use of two syringes in such environments—one for contrast medium and the other for flushing medium. Thus, it is contemplated that the present invention, in accordance with at least one presently preferred embodiment, could be utilized in such a context in that the operator could administer a protocol involving essentially any desired order of contrast medium and flushing medium phases.

A "pause" arrangement is also contemplated in accordance with at least one presently preferred embodiment of the present invention. A "pause" phase would essentially be similar to a "hold" phase in that it would represent a user-selected and programmed period of time in which no programmed injection of contrast medium or flushing medium is taking place. However, it would differ from a "hold" phase in the respect that it could essentially be a preprogrammed "hold" of limited duration that ends with an automatic transition to the next infusion phase (if any) in the protocol, whereas a "hold" phase would be of indefinite duration, with the protocol only to be reactivated by a manual prompt from the operator. Although "pause" phases have been known in conjunction with CT imaging arrangements, they are apparently not known in conjunction with MR imaging arrangements.

It should be appreciated that the inventive arrangements described hereinabove afford a degree of flexibility and versatility in programming an injection protocol than apparently has been hitherto realized. One distinct advantage inherent in such arrangements is their adaptability to foreseeable changes in the injection arts that may occur in the future, such as the development of new contrast media or increases in the efficiency of imaging scanners. For instance, it is conceivable that a different type of contrast medium might necessitate its injection into a patient via a much different protocol than might now normally be used with existing contrast media. Increases in imaging speed might also result in the need for vastly different types of protocols than are available on conventional equipment at present.

It will be appreciated that the flexibility and versatility achieved in accordance with at least one presently preferred embodiment of the present invention, with the use of an automatic arrangement, far outstrips any flexibility and versatility that might be gained through certain uses of existing injection arrangements. For example, although it is conceivable to employ two or more "SPECTRIS" systems for the purpose of executing a composite protocol, made up of separate protocols from the different systems, that might reflect a higher degree of versatility (e.g., by enabling the execution of a second contrast medium phase after a flushing medium phase), it will be appreciated that such an arrangement would be cumbersome, difficult to manage, and possibly inaccurate, in that one or more operators would need to ensure that one phase on one system starts immediately after another phase on another system. Manual injection is, of course, also possible, even to such an extent that different injections, representing distinctly different contrast medium and flushing medium phases, could be executed one after the other by one or more medical personnel. Again, though, such an arrangement would appear to prone to the potential of great inaccuracy, not only in terms of the timing of the successive injections but also in terms of the flowrates being used and the difficulty in keeping them constant over the duration of each phase (if indeed constant flowrates are desired).

Several other advantages would appear to be attainable in accordance with at least one presently preferred embodiment of the present invention. For example, an entire protocol can be stored and recalled for future use. The injector can reserve the flushing medium that is needed for an entire protocol and can alert the operator, before an injection commences, as to insufficient fluid volume. Moreover, in a multi-phased protocol that includes flushing and has an intermediate "hold" phase, the protocol can shut off flow in a "KVO" state automatically in order to preserve any necessary flushing medium for a subsequent pre-programmed flushing phase.

Although a maximum of six phases for one protocol has been described hereabove, it will be appreciated that the present invention broadly contemplates that no maximum on the number of phases in a protocol necessarily need be imposed.

Although all types of phases, especially contrast medium and flushing medium phases, have essentially been described hereinabove as being linear in nature (i.e., having a fixed flowrate over the duration of the phase), it should be understood that the present invention also broadly contemplates the programming and execution of phases that are not linear in nature. For example, it is conceivable that a contrast medium or flushing medium phase (and possibly even a "KVO" phase) could represent a non-linear function, in which the flowrate could possibly be variable over the duration of the phase and could be programmed in by means of an equation, lookup table or other suitable arrangement. In the case of "KVO", it is even conceivable that short "bursts" of flushing medium could be emitted at a variable rate instead of a fixed rate.

Although syringes have been specifically contemplated hereinabove for use in injection protocols, as a means for storing and administering contrasting medium or flushing medium, it is to be understood that other arrangements for this purpose are conceivable within the scope of the present invention, such as, for example, the use of peristaltic pumps.

In the context of the present disclosure, the terms "infusion" and "injection", and their grammatical derivations, are to be construed as being interchangeable and are meant to refer to essentially any of a wide range of arrangements for introducing fluid into a patient.

If not otherwise stated herein, it may be assumed that all components and/or processes described heretofore may, if appropriate, be considered to be interchangeable with similar components and/or processes disclosed elsewhere in the specification, unless an express indication is made to the contrary.

If not otherwise stated herein, any and all patents, patent publications, articles and other printed publications discussed or mentioned herein are hereby incorporated by reference as if set forth in their entirety herein.

It should be appreciated that the apparatus and method of the present invention may be configured and conducted as appropriate for any context at hand. The embodiments described above are to be considered in all respects only as illustrative and not restrictive. The scope of the invention is defined by the following claims rather than the foregoing description. All changes which come within the meaning and range of equivalency of the claims are to be embraced within their scope.

What is claimed is:

1. A fluid injection apparatus comprising:
   at least one drive mechanism;
   at least two fluid containers operably associated with the at least one drive mechanism, one fluid container containing a contrast medium and the other fluid container containing a flushing medium; and
   a control device operably associated with the at least one drive mechanism, the control device operable to selectively program a plurality of phases of an injection procedure, each of the plurality of phases comprising at least one of a contrast medium phase, a flushing medium phase and a KVO phase.

2. The apparatus of claim 1 wherein at least one of the two fluid containers comprises a syringe.

3. The apparatus of claim 1 wherein the first phase comprises a flushing medium phase and the second phase comprises a contrast medium phase.

4. The apparatus of claim 1 wherein the phases are defined by at least two injection parameters selected from fluid flow rate, fluid volume and injection duration.

5. A fluid injection apparatus comprising:
   at least one drive mechanism;
   at least one fluid container operably associated with the at least one drive mechanism; and
   a control device operably associated with the at least one drive mechanism, the control device operable to selectively program at least two phases of an injection procedure, the first phase comprising one of at least a contrast medium phase and a flushing medium phase and the second phase comprising a hold phase, wherein KVO occurs during the hold phase.

6. The apparatus of claim 5 wherein the hold phase is of indefinite duration.

7. The apparatus of claim 5 wherein the hold phase allows an operator to modify one or more injection parameters of a subsequent phase.

8. The apparatus of claim 5 wherein the at least one fluid container comprises a syringe.

9. A fluid injection apparatus comprising:
   at least one drive mechanism;
   at least two fluid containers operably associated with the at least one drive mechanism, one fluid container containing a contrast medium and the other fluid container containing a flushing medium; and
   a control device operably associated with the at least one drive mechanism, said control device comprising:
      means for programming a first phase of an injection procedure;
      means for programming a second phase of an injection procedure, subsequent to a first phase of an injection procedure; and
      means for programming a third phase of an injection procedure, subsequent to a second phase of an injection procedure, as a phase other than a flushing medium phase.

10. The apparatus of claim 9, wherein said means for programming a first phase of an injection procedure comprises means for programming a first phase of an injection procedure as a phase other than a contrast medium phase.

11. The apparatus of claim 10, wherein said means for programming a first phase of an injection procedure comprises means for programming a first phase of an injection procedure as a contrast medium phase.

12. The apparatus of claim 9, wherein said means for programming a second phase of an injection procedure comprises:
   means for programming a second phase of an injection procedure, subsequent to a first phase of an injection procedure, as a contrast medium phase; and
   means for programming a second phase of an injection procedure, subsequent to a first phase of an injection procedure, as a flushing medium phase.

13. The apparatus of claim 9, wherein said control device further comprises means for programming a third phase of an injection procedure as a flushing medium phase.

14. The apparatus of claim 9, wherein said means for programming a second phase of an injection procedure comprises means for programming a second phase of an injection procedure, subsequent to a first phase of an injection procedure, as a hold phase.

15. The apparatus of claim 9, wherein said control device further comprises means for programming a pause phase to occur between first and second phases of an injection procedure.

16. A fluid injection apparatus comprising:
at least one drive mechanism;
at least two fluid containers operably associated with the at least one drive mechanism, one fluid container containing a contrast medium and the other fluid container containing a flushing medium; and
a control device operably associated with the at least one drive mechanism, said control device comprising:
means for programming a first phase of an injection procedure;
means for programming a second phase of an injection procedure, subsequent to a first phase of an injection procedure;
means for programming a third phase of an injection procedure, subsequent to a second phase of an injection procedure; and
means for programming a fourth phase of an injection procedure, subsequent to a second phase of an injection procedure, as a phase other than a flushing medium phase.

17. The apparatus of claim 16, wherein said means for programming a first phase of an injection procedure comprises means for programming a first phase of an injection procedure as a phase other than a contrast medium phase.

18. The apparatus of claim 17, wherein said means for programming a first phase of an injection procedure comprises means for programming a first phase of an injection procedure as a contrast medium phase.

19. The apparatus of claim 16, wherein said means for programming a second phase of an injection procedure comprises:
means for programming a second phase of an injection procedure, subsequent to a first phase of an injection procedure, as a flushing medium phase; and
means for programming a second phase of an injection procedure, subsequent to a first phase of an injection, as a flushing medium phase.

20. The apparatus of claim 16, wherein said means for programming a third phase of an injection procedure comprises:
means for programming a third phase of an injection procedure, subsequent to a second phase of an injection procedure, as a contrast medium phase; and
means for programming a third phase of an injection procedure, subsequent to a second phase of an injection procedure, as a flushing medium phase.

21. The apparatus of claim 16, wherein said control device further comprises means for programming a fourth phase of an injection procedure, subsequent to a third phase of an injection procedure, as a flushing medium phase.

22. The apparatus of claim 16, further comprising means for programming a second phase of an injection procedure, subsequent to a first phase of an injection procedure, as a hold phase.

23. The apparatus of claim 16, wherein said control device further comprises:
means for programming a second phase of an injection procedure, subsequent to a first phase of an injection procedure; and
means for programming a pause phase to occur between first and second phases of an injection procedure.

24. A fluid injection apparatus comprising:
at least one drive mechanism;
at least two fluid containers operably associated with the at least one drive mechanism, one fluid container containing a contrast medium and the other fluid container containing a flushing medium; and
a control device operably associated with the at least one drive mechanism, said control device comprising means for programming a first phase of an injection procedure as a phase other than a contrast medium phase.

25. The apparatus of claim 24, wherein said control device further comprises means for programming a first phase of an injection procedure as a contrast medium phase.

26. The apparatus of claim 24 wherein at least one of the two fluid containers comprises a syringe.

27. The apparatus of claim 24 wherein said means for programming a first phase of an injection procedure as a phase other than a contrast medium phase comprises means for programming a first phase of an injection procedure as a flushing medium phase.

28. The apparatus of claim 24, wherein said control device further comprises means for programming a second phase of an injection procedure, subsequent to a first phase of an injection procedure, as a contrast medium phase.

29. The apparatus of claim 24, wherein said control device further comprises means for defining at least one phase of an injection procedure by at least two injection parameters selected from fluid flow rate, fluid volume and injection duration.

30. The apparatus of claim 24, wherein said control device further comprises means for defining each phase of an injection procedure by at least two injection parameters selected from fluid flow rate, fluid volume and injection duration.

31. The apparatus of claim 24 wherein said control device further comprises:
means for programming a first phase of an injection procedure as a KVO phase.

32. The apparatus of claim 24 wherein said control device further comprises means for programming a second phase of an injection procedure, subsequent to a first phase of an injection procedure, as a flushing medium phase.

33. The apparatus of claim 24 wherein said control device further comprises means for programming a second phase of an injection procedure, subsequent to a first phase of an injection procedure, as a KVO phase.

34. The apparatus of claim 24, further comprising means for programming a second phase of an injection procedure, subsequent to a first phase of an injection procedure, as a hold phase.

35. The apparatus of claim 34 wherein said means for programming a second phase of an injection procedure as a hold phase comprises means for establishing a hold phase of indefinite duration.

36. The apparatus of claim 35 wherein said means for programming a second phase of an injection procedure as a hold phase comprises means for establishing KVO during a hold phase.

37. The apparatus of claim 34, wherein said control device further comprises means for facilitating, during a hold phase, modification of one or more injection parameters of a subsequent phase.

38. The apparatus of claim 24, wherein said control device further comprises:
means for programming a second phase of an injection procedure, subsequent to a first phase of an injection procedure; and
means for programming a pause phase to occur between first and second phases of an injection procedure.

39. The apparatus of claim 38, wherein said means for programming a first phase of an injection procedure as a phase other than a contrast medium phase comprises means for programming a first phase of an injection procedure as a flushing medium phase.

40. The apparatus of claim 38, wherein said means for programming a second phase of an injection procedure comprises:
means for programming a second phase of an injection procedure, subsequent to a first phase of an injection procedure, as a contrast medium phase; and
means for programming a second phase of an injection procedure, subsequent to a first phase of an injection procedure, as a flushing medium phase.

41. The apparatus of claim 38 wherein said means for programming a pause phase comprises means for establishing a pause phase for a fixed duration of time.

42. The apparatus of claim 38 wherein said control device comprises means for automatically commencing a second phase of an injection procedure after the end of a pause phase.

43. A fluid injection apparatus comprising:
at least one drive mechanism;
at least one fluid container operably associated with the at least one drive mechanism; and
a control device operably associated with the at least one drive mechanism, said control device comprising:
means for programming a first phase of an injection procedure as a contrast medium phase;
means for programming a first phase of an injection procedure as a flushing medium phase; and
means for programming a second phase of an injection procedure, subsequent to a first phase of an injection procedure, as a hold phase.

44. A fluid injection apparatus comprising:
at least one drive mechanism;
at least one fluid container operably associated with the at least one drive mechanism; and
a control device operably associated with the at least one drive mechanism, said control device comprising:
means for programming a first phase of an injection procedure as a contrast medium phase;
means for programming a first phase of an injection procedure as a flushing medium phase;
means for programming a second phase of an injection procedure as a contrast medium phase;
means for programming a second phase of an injection procedure as a flushing medium phase; and
means for programming a pause phase to occur between first and second phases of an injection procedure.

45. A fluid injection apparatus comprising:
at least one drive mechanism;
at least two fluid containers operably associated with the at least one drive mechanism, one fluid container containing a contrast medium and the other fluid container containing a flushing medium; and
a control device operably associated with the at least one drive mechanism, said control device comprising means for establishing a first phase of an injection procedure as a phase other than a contrast medium phase.

46. A fluid injection apparatus comprising:
at least one drive mechanism;
at least two fluid containers operably associated with the at least one drive mechanism, one fluid container containing a contrast medium and the other fluid container containing a flushing medium; and
a control device operably associated with the at least one drive mechanism, said control device comprising an arrangement for programming a first phase of an injection procedure as a phase other than a contrast medium phase.

47. A fluid injection apparatus comprising:
at least one drive mechanism;
at least two fluid containers operably associated with the at least one drive mechanism, one fluid container containing a contrast medium and the other fluid container containing a flushing medium; and
a control device operably associated with the at least one drive mechanism, said control device comprising an arrangement for establishing a first phase of an injection procedure as a phase other than a contrast medium phase.

48. A method of programming an injection apparatus comprising a drive mechanism, at least two fluid containers and a control device for programming the injection procedure, the method comprising:
selectively programming a plurality of phases of an injection procedure, each of the plurality of phases comprising at least one of a contrast medium phase, a flushing medium phase and a KVO phase.

49. A method of programming an injection apparatus comprising a drive mechanism, at least two fluid containers and a control device for programming the injection procedure, the method comprising:
selectively programming at least two phases of an injection procedure, the first phase comprising one of at least a contrast medium phase and a flushing medium phase and the second phase comprising a hold phase, wherein KVO occurs during the hold phase.

50. A method of programming an injection procedure, comprising:
providing an injection apparatus comprising a drive mechanism, at least two fluid containers and a control device for programming the injection procedure;
selectively programming a first phase of the injection procedure, the first phase comprising one of a contrast medium phase and a flushing medium phase;
selectively programming at least a subsequent second phase of the injection procedure, the second phase comprising one of a contrast medium phase and a flushing medium phase; and
selectively programming a KVO phase.

51. A method of programming an injection procedure comprising:
programming a first phase of an injection procedure;
programming a second phase of an injection procedure to occur subsequent to the first phase; and programming a third phase of an injection procedure, to occur subsequent to the second phase, as a phase other than a flushing medium phase.

52. The method of claim 51, wherein said step of programming a first phase of an injection procedure comprises selectably programming the first phase of an injection procedure as a phase other than a contrast medium phase.

53. The method of claim 52, wherein said step of programming a first phase comprises selectably programming the first phase as a contrast medium phase.

54. The method of claim 51, wherein said step of programming a second phase comprises selectably programming the second phase as a contrast medium phase.

55. The method of claim 51, wherein said step of programming a second phase comprises selectably programming the second phase as a flushing medium phase.

56. The method of claim 51, wherein:
said step of programming a third phase is performed during one protocol; and
said method further comprises, during another protocol, the step of selectably programming a third phase of an injection procedure as a flushing medium phase.

57. The method of claim 51, wherein said step of programming a second phase of an injection procedure comprises selectably programming the second phase as a hold phase.

58. The method of claim 51, further comprising the step of programming a pause phase to occur between first and second phases of an injection procedure.

59. A method of programming an injection procedure comprising:
programming a first phase of an injection procedure;
programming a second phase of an injection procedure to occur subsequent to the first phase;
programming a third phase of an injection procedure to occur subsequent to the second phase; and
programming a fourth phase of an injection procedure, to occur subsequent to the third phase, as a phase other than a flushing medium phase.

60. The method of claim 59, wherein said step of programming a first phase of an injection procedure comprises selectably programming the first phase of an injection procedure as a phase other than a contrast medium phase.

61. The method of claim 59, wherein said step of programming a first phase comprises selectably programming the first phase as a contrast medium phase.

62. The method of claim 59, wherein said step of programming a second phase comprises selectably programming the second phase as a contrast medium phase.

63. The method of claim 59, wherein said step of programming a second phase comprises selectably programming the second phase as a flushing medium phase.

64. The method of claim 59, wherein said step of programming a third phase comprises selectably programming the third phase as a contrast medium phase.

65. The method of claim 59, wherein said step of programming a third phase comprises selectably programming the third phase as a flushing medium phase.

66. The method of claim 59, wherein:
said step of programming a fourth phase is performed during one protocol; and
said method further comprises, during another protocol, the step of selectably programming a fourth phase of an injection procedure as a flushing medium phase.

67. The method of claim 59, wherein said step of programming a second phase of an injection procedure comprises selectably programming the second phase as a hold phase.

68. The method of claim 59, further comprising the step of programming a pause phase to occur between first and second phases of an injection procedure.

69. A method of programming an injection procedure comprising: programming a first phase of an injection procedure as a phase other than a contrast medium phase.

70. The method of claim 69, wherein:
said step of programming a first phase is performed during one protocol; and
said method further comprises, during another protocol, the step of selectably programming a first phase of an injection procedure as a contrast medium phase.

71. The method of claim 69, further comprising the step of programming a KVO phase.

72. The method of claim 69, further comprising the step of programming a second phase of an injection procedure, to occur subsequent to a first phase of an injection procedure, as a hold phase.

73. The method of claim 69, further comprising the step of modifying, during said hold phase, one or more injection parameters of a subsequent phase.

74. The method of claim 69, further comprising:
programming a second phase of an injection procedure to occur subsequent to the first phase of an injection procedure; and
programming a pause phase to occur between first and second phases of an injection procedure.

75. The method of claim 74, wherein said step of programming a first phase comprises selectably programming the first phase as a flushing medium phase.

76. The method of claim 74, wherein said step of programming a second phase comprises selectably programming the second phase as a contrast medium phase.

77. The method of claim 74, wherein said step of programming a second phase comprises selectably programming the second phase as a flushing medium phase.

78. The method of claim 74 wherein said step of programming a pause phase comprises establishing said pause phase for a fixed duration of time.

79. A method of programming an injection procedure, comprising:
selectably programming a first phase of an injection procedure, during a first protocol, as a contrast medium phase;
selectably programming a first phase of an injection procedure, during a second protocol, as a flushing medium phase; and
programming a second phase of an injection procedure, subsequent to the first phase during at least one of said first and second protocols, as a hold phase.

80. A method of programming an injection procedure, comprising:
selectably programming a first phase of an injection procedure, during a first protocol, as a contrast medium phase; selectably programming a first phase of an injection procedure, during a second protocol, as a flushing medium phase;
selectably programming a second phase of an injection procedure, during one of said first and second protocols, as a contrast medium phase;
selectably programming a second phase of an injection procedure, during one of said first and second protocols, as a flushing medium phase; and
programming a pause phase to occur between first and second phases of an injection procedure, during at least one of said first and second protocols.

* * * * *

UNITED STATES PATENT AND TRADEMARK OFFICE
CERTIFICATE OF CORRECTION

PATENT NO. : 6,339,718 B1
DATED : January 15, 2002
INVENTOR(S) : Zatezalo et al.

It is certified that error appears in the above-identified patent and that said Letters Patent is hereby corrected as shown below:

<u>Title page,</u>
Item [74], *Attorney, Agent, or Firm,* line 1, delete "George" and replace with
-- Gregory --.

<u>Column 11,</u>
Line 46, delete "flushing" and replace with -- contrast --.
Line 48, "first phase of an injection" insert -- procedure --.

Signed and Sealed this

Twentieth Day of August, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,339,718 B1
DATED         : January 15, 2002
INVENTOR(S)   : Zatezalo et al.

It is certified that error appears in the above-identified patent and that said Letters Patent is hereby corrected as shown below:

Title page,
Item [74], *Attorney, Agent, or Firm,* line 1, delete "George" and replace with
-- Gregory --.

Column 11,
Line 46, delete "flushing" and replace with -- contrast --.
Line 48, after "first phase of an injection" insert -- procedure --.

This certificate supersedes Certificate of Correction issued August 20, 2002.

Signed and Sealed this

Twenty-fifth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,339,718 B2
APPLICATION NO. : 09/365278
DATED : January 15, 2002
INVENTOR(S) : Zatezalo It is certified that error appears in the above-identified patent and that said Letters Patent is hereby corrected as shown below:

On the Title Page, in Field (56), under "REFERENCES CITED", insert --5,806,519  09/1998  Evans III, et al.--

On the Title Page, in Field (56), under "REFERENCES CITED", insert --4,710,166  12/1987  Thomson, et al.--

On the Title Page, in Field (56), under "REFERENCES CITED", insert --5,304,126  04/1994  Epstein, et al.--

On the Title Page, in Field (56), under "REFERENCES CITED", insert --4,553,958  11/1985  LeCocq.--

On the Title Page, in Field (56), under "REFERENCES CITED", insert --5,782,805  07/1998  Meinzer, et al.--

On the Title Page, in Field (56), under "REFERENCES CITED", insert --4,006,736  02/1977  Kranys, et al.--

On the Title Page, in Field (56), under "REFERENCES CITED", insert --4,677,980  07/1987  Reilly, et al.--

On the Title Page, in Field (56), under "REFERENCES CITED", insert --5,383,858  01/1995  Reilly, et al.--

On the Title Page, in Field (56), under "REFERENCES CITED", insert --0192786  09/1986  Reilly, et al.--

On the Title Page, in Field (56), under "REFERENCES CITED", insert --0302752  02/1989  Orkin, et al.--

Signed and Sealed this
First Day of March, 2011

David J. Kappos
*Director of the United States Patent and Trademark Office*

CERTIFICATE OF CORRECTION (continued)
U.S. Pat. No. 6,339,718 B2

On the Title Page, in Field (56), under "OTHER PUBLICATIONS", in Column 2, Line 8, delete "Injector" and insert --Injection--, therefor.

On the Title Page, in Field (56), under "OTHER PUBLICATIONS", insert --MCT/MCT Plus Operation Manual (1991), KMP 810P Rev. B.--

On the Title Page, in Field (56), under "OTHER PUBLICATIONS", insert --Medrad Spectris MR Injector Operation Manual (1996), 92901-T-107, Rev. E.--

On the Title Page, in Field (56), under "OTHER PUBLICATIONS", insert --Medrad Envision CT Injector Operation Manual (1995), 92401-T-123, Rev. E.--

In the Specification, Column 16, Line 18, delete "69" and insert --72--.